United States Patent
Pröpster et al.

(10) Patent No.: US 10,745,319 B2
(45) Date of Patent: Aug. 18, 2020

(54) METHOD TO INCREASE THE STRENGTH OF A FORM BODY OF LITHIUM SILICATE GLASS CERAMIC

(71) Applicant: DENTSPLY SIRONA Inc., York, PA (US)

(72) Inventors: Michael Pröpster, Bruchköbel (DE); Markus Vollmann, Gelnhausen (DE)

(73) Assignee: DENTSPLY SIRONA Inc., York, PA (US)

( * ) Notice: Subject to any disclaimer, the term of this patent is extended or adjusted under 35 U.S.C. 154(b) by 423 days.

(21) Appl. No.: 15/160,678

(22) Filed: May 20, 2016

(65) Prior Publication Data
US 2016/0340239 A1 Nov. 24, 2016

(51) Int. Cl.
| | |
|---|---|
| C03B 32/00 | (2006.01) |
| C03C 21/00 | (2006.01) |
| C03C 4/00 | (2006.01) |
| C03C 3/097 | (2006.01) |
| A61K 6/804 | (2020.01) |
| A61K 6/818 | (2020.01) |
| A61K 6/822 | (2020.01) |
| A61K 6/833 | (2020.01) |
| A61K 6/853 | (2020.01) |
| C03B 25/00 | (2006.01) |

(Continued)

(52) U.S. Cl.
CPC ............ *C03C 21/002* (2013.01); *A61K 6/804* (2020.01); *A61K 6/818* (2020.01); *A61K 6/822* (2020.01); *A61K 6/833* (2020.01); *A61K 6/853* (2020.01); *C03B 25/00* (2013.01); *C03C 3/097* (2013.01); *C03C 4/0021* (2013.01); *C03C 10/0027* (2013.01); *C03C 17/22* (2013.01); *C03C 2204/00* (2013.01)

(58) Field of Classification Search
CPC ................................. C03B 32/00; C03C 21/00
See application file for complete search history.

(56) References Cited

U.S. PATENT DOCUMENTS

| 3,357,876 A | 12/1967 | Rinehart |
| 4,212,919 A * | 7/1980 | Hoda ........................ C03C 3/11 |
| | | 428/410 |

(Continued)

FOREIGN PATENT DOCUMENTS

| BE | 618738 A | 12/1962 |
| CA | 2911284 A1 | 11/2014 |

(Continued)

OTHER PUBLICATIONS

Fischer et al, Biomed. Mater. Rs; 87A: 582-587, 2008 "Chemical Strengthening of a dental lithium disilicate glass-ceramic material".

(Continued)

*Primary Examiner* — Cynthia Szewczyk
(74) *Attorney, Agent, or Firm* — Dentsply Sirona Inc.

(57) ABSTRACT

The invention relates to a method to produce a medical form body of lithium silicate glass ceramic. To increase its strength it is proposed that a surface compressive stress is created in a form body of lithium silicate glass, or containing lithium silicate glass, through the replacement of lithium ions by alkali metal ions of greater diameter. For this purpose the form body is covered with a paste that contains alkali metal.

11 Claims, 1 Drawing Sheet

(51) Int. Cl.
*C03C 10/00* (2006.01)
*C03C 17/22* (2006.01)

(56) References Cited

U.S. PATENT DOCUMENTS

| | | | |
|---|---|---|---|
| 4,546,006 A | 10/1985 | Ohno | |
| 4,784,606 A | 11/1988 | Jones | |
| 5,705,273 A * | 1/1998 | Denry | C03C 21/008 427/2.27 |
| 6,703,590 B1 | 3/2004 | Holley | |
| 2003/0099062 A1* | 5/2003 | Kataoka | C03C 10/0027 360/99.12 |
| 2004/0221615 A1* | 11/2004 | Postupack | C03C 21/002 65/30.14 |
| 2009/0100873 A1* | 4/2009 | Allan | C03B 17/064 65/85 |
| 2012/0052302 A1* | 3/2012 | Matusick | C03C 15/00 428/410 |
| 2012/0135195 A1* | 5/2012 | Glaesemann | B23K 26/073 428/156 |
| 2012/0236526 A1* | 9/2012 | Weber | C03C 21/002 361/807 |
| 2013/0295523 A1 | 11/2013 | Durschang | |
| 2015/0104655 A1 | 4/2015 | Kim | |
| 2016/0340239 A1 | 11/2016 | Propster | |

FOREIGN PATENT DOCUMENTS

| | | |
|---|---|---|
| DE | 2401275 A1 | 7/1974 |
| DE | 3015529 A1 | 11/1980 |
| DE | 19750794 A1 | 6/1999 |
| DE | 102009060274 A1 | 6/2011 |
| DE | 202011110343 U1 | 9/2013 |
| DE | 10336913 B4 | 1/2014 |
| EP | 2662342 A1 | 11/2013 |
| EP | 3053886 A1 | 8/2016 |
| FR | 2454796 A1 | 11/1980 |
| WO | 2012175450 A1 | 12/2012 |
| WO | 2012175615 A1 | 12/2012 |
| WO | 2013053865 A2 | 4/2013 |

OTHER PUBLICATIONS

W. Holand, G. Beall; "Glass-Ceramic Technology, 2002"; pp. 291-292.
International Search Report; PCT/EP2016/061460; Jul. 14, 2016 (completed); dated Jul. 22, 2016.
Written Opinion of the International Searching Authority; PCT/EP2016/061460; Jul. 14, 2016 (completed); dated Jul. 22, 2016.
International Preliminary Report on Patentability; PCT/EP2016/061460; Jul. 14, 2016 (completed); dated Jul. 22, 2016.
I.L. Dentry et. al.; Enhanced Chemical Strengthening of Feldspathic Dental Porcelain; J. Dent Res; Oct. 1993; pp. 1429-1433.
R.R. Seghi et. al.; Effects of Ion Exchange on Hardness and Fracture Toughness of Dental Ceramics; The International Journal of Prosthodontics, vol. 5, No. 4, 1992; pp. 309-314.
European Search Report; EP16170624; Jul. 12, 2016 (completed).

* cited by examiner

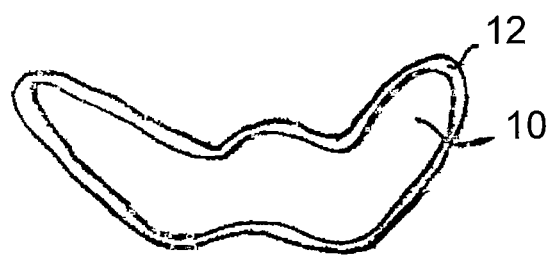

METHOD TO INCREASE THE STRENGTH OF A FORM BODY OF LITHIUM SILICATE GLASS CERAMIC

THE CROSS-REFERENCE TO RELATED APPLICATIONS

This patent application claims the benefit of and priority to German Patent Application No. 10 2015 108 171.7, filed on May 22, 2015, which is herein incorporated by reference for all purposes.

TECHNICAL FIELD

The invention relates to a method to increase the strength of a medical form body comprising a lithium silicate glass ceramic, preferably in the form of a dental form body, or a part of such a body, in particular a bridge, crown, coping, inlay, onlay or veneer.

BACKGROUND OF THE INVENTION

The use of blanks of lithium silicate glass ceramic in dental technology for the production of dental restorations has been proven because of their light-optical characteristics and their strength and biocompatibility. Heat treatment results in a final crystallization of the glass ceramic to yield good optical qualities and sufficient chemical stability in particular. Corresponding methods are disclosed in, for example, DE 197 50 794 A1 or DE 103 36 913 B4.

To achieve a high strength and at the same time a good translucency, at least one stabilizer from the group zirconium oxide, hafnium oxide or a mixture thereof, in particular zirconium oxide, is added to the raw starting materials in the form of lithium carbonate, quartz, aluminum oxide etc., i.e., the usual starting components. Attention is drawn here, for example, to DE 10 2009 060 274 A1, WO 2012/175450 A1, WO 2012/175615 A1, WO 2013/053865 A2 or EP 2 662 342 A1. Machining of these zirconium oxide containing lithium silicates is also possible in the final crystallized state.

The publications of I. L. Denry et. al., Enhanced Chemical Strengthening of Feldspathic Dental Porcelain, J Dent Res, October 1993, pages 1429 to 1433, and R. R. Seghi et. al., Effects of Ion Exchange on Hardness and Fracture Toughness of Dental Ceramics, The International Journal of Prosthodontics, Volume 5, No. 4, 1992, pages 309 to 314, disclose studies of composite ceramics which are comprised of feldspathic glass types in which leucite precipitates may be present. To increase strength, it was proposed to replace sodium ions by lithium ions and then to replace lithium ions by potassium ions in a two-step process. Smaller ions can also be replaced by rubidium ions. This enabled an increase in strength of up to a maximum of 80% if rubidium oxide was used. Rubidium, however, has the disadvantage that the heat expansion coefficient of the ceramics is increased.

DE 30 15 529 A1 discloses a method to improve the mechanical strength of dental porcelain. In this method a restoration is coated with enamel so that there is an exchange of alkali ions in the enamel. For this purpose the restoration is immersed in a bath of melted salt at a temperature between 200° C. and the transition point of the enamel.

U.S. Pat. No. 4,784,606 A discloses a dental brace of glass, the strength of which is increased by ion exchange.

A method for increasing the hardness of a silicate glass object, such as a bottle is disclosed in DE 24 01 275 A1 the object is preferably heated to at least 370° C. and is sprayed with a pulverized mixture of alkali metal salts. This enables ion exchange which increases strength.

SUMMARY OF THE INVENTION

In one aspect, the present invention is directed to a method to increase the strength of a medical form body of lithium silicate glass ceramic comprising the steps of: creating a surface compressive stress in the form body of lithium silicate glass ceramic through the replacement of lithium ions by alkali metal ions of greater diameter; coating at least a portion of the form body with a paste having one or more alkali metals, wherein the at least portion of the form body is in contact with the paste for a time t at a temperature T; and removing the paste from the form body.

In another aspect, the present invention is directed to a form body in the form of a medical or dental object or a part thereof, of lithium silicate glass ceramic, comprises a surface compressive stress that is generated in the form body through the replacement of lithium ions by alkali ions of greater diameter.

In yet another aspect, it is contemplated that the of the present invention has one or any combination of the following features: wherein the coating step, the form body is coated with a viscous solution or dispersion of a salt containing the alkali metal ions as the paste; wherein the coating step, the paste is applied to the form body by spraying on to the form body; further comprising the step of mixing a salt with at least one substance selected from the group consisting of 1,4-butanediol, hexanetriol, and a mixture of the two substances to form the paste; wherein the coating step, the paste is applied to all surfaces of the form body with a thickness D of not less than 0.5 mm; wherein alkali metal ions are selected from the group consisting of Na, K, Cs, Rb ions and combinations thereof to generate the surface compressive stress; wherein the paste includes potassium ions, sodium ions or a combination of both potassium ions and sodium ions; wherein the forming step, the form body that is in contact with the paste at a temperature T where T≥300° C. for a time t; further comprising the step of forming the form body or a blank from a glass melt that includes at least the following as starting components: $SiO_2$, $A_2O_3$, $Li_2O$, $K_2O$, at least one nucleating agent, and at least one stabilizer; wherein the glass melt further includes at least one coloring metal oxide; further comprising the step of forming the form body or a blank from a glass melt that includes the following components in percentage by weight:

| | |
|---|---|
| $SiO_2$ | 50-80, | at least one nucleating ent 0.5-11,

| | |
|---|---|
| $Al_2O_3$ | 0-10, |
| $Li_2O$ | 10-25, |
| $K_2O$ | 0-13, |
| $Na_2O$ | 0-1, |
| $ZrO_2$ | 0-20, |
| $CeO_2$ | 0-10, |
| $Tb_4O_7$ | 0-8, | optionally an oxide or a number of oxides of an earth alkali metal or a number of earth alkali metals selected from the group consisting of magnesium, calcium, strontium, and barium 0-20, optionally one or more additives selected from the group consisting of $B_2O_3$, $MnO_2$, $Fe_2O_3$, $V_2O_5$, $TiO_2$, $Sb_2O_3$, ZnO, $SnO_2$ and fluorides 0-6, optionally one or more oxides of the rare earth metals with the atomic numbers 57, 59-64, 66-71, 0-5; wherein the glass melt includes the following as starting components in percentage by weight

| | |
|---|---|
| $SiO_2$ | 58.1 ± 2.0 |
| $P_2O_5$ | 5.0 ± 1.5 |
| $Al_2O_3$ | 4.0 ± 2.5 |
| $Li_2O$ | 16.5 ± 4.0 |
| $K_2O$ | 2.0 ± 0.2 |
| $ZrO_2$ | 10.0 ± 0.5 |
| $CeO_2$ | 0-3, |
| $Tb_4O_7$ | 0-3, |
| $Na_2O$ | 0-0.5. | wherein the forming step, the blank is formed from the glass melt in the course of cooling or following cooling to room temperature, said blank then being subject to at least one first heat treatment W1 at a temperature $T_{W1}$ for a time $t_{W1}$, wherein 620° C.$\leq T_{W1} \leq$800° C., and/or 1 minute$\leq t_{W1} \leq$200 minutes; wherein the forming step, the first heat treatment W1 is carried out in two steps, wherein in particular in a first step a temperature $T_{S1}$ is set where 630° C.$\leq T_{S1} \leq$690° C. and/or in a second step a temperature $T_{S1}$ where 720° C.$\leq T_{S2}$ 780° C. and/or a heating rate $A_{S1}$ up to the temperature $T_{S1}$ is 1.5 K/minute$\leq A_{S1} \leq$2.5 K/minute and/or a heating rate $A_{S2}$ up to the temperature $T_{S2}$ is 8 K/minutes$\leq T_{S2} \leq$12 K/minute; wherein the forming step, the lithium silicate glass ceramic blank is subjected, after the first heat treatment W1, to a second heat treatment W2 at a temperature $T_{W2}$ for a time $t_{W2}$, wherein 800° C.$\leq T_{W2} \leq$1040° C., and/or 2 minutes$\leq t_{W2} \leq$200 minutes; wherein the forming step, after the first or second heat treatment step, the form body is prepared from the blank through grinding and/or milling or pressing, wherein the heat treatment step or steps is/are carried out during or after pressing; wherein the alkali metal ions are selected from the group consisting of Na, K, Cs, ions, and combinations of ions thereof; wherein a glass phase of the form body or a blank from which the form body is prepared from, includes at least one stabilizer that increases the strength of the form body, the concentration of which in the starting composition of the form body is 8-12% by weight; wherein the form body is prepared from a glass melt that contains the following components in percentage by weight

| | |
|---|---|
| $SiO_2$ | 52-70, |
| $P_2O_5$ | 0.5-11, |
| $Al_2O_3$ | 0.5-5, |
| $Li_2O$ | 13-22, |
| $K_2O$ | 0.5-8, |
| $Na_2O$ | 0-0.5, |
| $ZrO_2$ | 4-16, |
| $CeO_2$ | 0.5-8, |
| $Tb_4O_7$ | 0.5-6, | optionally an oxide or a number of oxides of an earth alkali metal or a number of earth alkali metals selected from the group consisting of magnesium, calcium, strontium, and barium 0-20, optionally one or more additives selected from the group consisting of $B_2O_3$, $MnO_2$, $Fe_2O_3$, $V_2O_5$, $TiO_2$, $Sb_2O_3$, ZnO, $SnO_2$ and fluorides 0-6, optionally one or more oxides of the rare earth metals with the atomic numbers 57, 59-64, 66-71 0-5; wherein the form body is prepared from a glass melt that contains the following components in percentage by weight:

| | |
|---|---|
| $SiO_2$ | 58.1 ± 2.0 |
| $P_2O_5$ | 5.0 ± 1.5 |
| $Al_2O_3$ | 4.0 ± 2.5 |
| $Li_2O$ | 16.5 ± 4.0 |
| $K_2O$ | 2.0 ± 0.2 |
| $ZrO_2$ | 10.0 ± 0.5 |
| $CeO_2$ | 1.5 ± 0.6 |
| $Tb_4O_7$ | 1.2 ± 0.4, |
| $Na_2O$ | 0.2-0.5. | wherein the form body has a glass phase in the range 20-65% by volume; wherein the form body contains lithium silicate crystals between 35% and 80% by volume of the body; wherein the percentage of alkali ions replacing the lithium ions, commencing from a surface of the form body down to a depth of 10 μm is in the range 5-20% by weight, and/or at a depth between 8 and 12 μm from the surface the percentage of alkali ions is in the range 5-10% by weight, and/or at a layer depth of between 12 and 14 μm from the surface the percentage of alkali ions is in the range 4-8% by weight, and/or at a depth from the surface between 14 and 18 μm the percentage of alkali ions is in the range 1-3% by weight; se of a paste containing at least one alkali metal salt for coating a form body of lithium silicate glass ceramic material, according to the methods of the present invention; or any combination thereof.

BRIEF DESCRIPTION OF THE DRAWINGS

FIG. 1 shows a cross-sectional view of a crown with a paste material of the present invention.

DETAILED DESCRIPTION OF THE INVENTION

The object of the invention is to develop a method of the aforementioned type so that the strength of the form body can be increased using simple process technology measures.

A further object is for untrained persons to be able to increase the strength to the desired degree.

The object of the invention is substantially solved in that a surface compressive stress is created in the form body of lithium silicate glass ceramic through the replacement of lithium ions by alkali metal ions of greater diameter, in that the form body is covered with a paste containing alkali metals, that the form body is in contact with the paste for a time t at a temperature T and that the paste is then removed from the form body.

The paste is thereby applied to the form body which is at a temperature that in principle corresponds to room temperature. The form body is then heated with the paste applied to a temperature T≥300° C., in particular 350° C.$\leq$T$\leq$600° C.

Sodium and/or potassium ions are preferably used as alkali ions to create the surface compressive stress.

It was found that when the lithium ions present in the form body of lithium silicate glass ceramic are replaced by Na/K ions that a pre-stress is created to a degree and thus a surface compressive stress, resulting in a substantial increase in strength. It was surprisingly found that even very short annealing times of less than one hour will lead to a substantial increase in strength. This is in clear contrast to conventional dental lithium silicate glass ceramics (e.max CAD from the firm Ivoclar), for which no strength-increasing effect is seen if lithium ions are replaced by sodium ions. Even with the described glass ceramic the effect is not seen to the same degree, as is apparent from Examples 1 and 2 below.

According to the invention the form body is enveloped by a paste which contains alkali metal ions, in particular Na ions and/or K ions, to the desired degree for a period of time t, i.e., the form body is covered with a paste layer to facilitate the desired replacement of lithium ions by Na ions or K ions of greater diameter, so that the desired surface compressive stress is built up and thus an increase in strength results.

Independently thereof, the required ion exchange in the surface region is particularly good if the form body is in contact with a corresponding paste at a temperature T≥300° C., in particular 350° C.≤T≤600° C., preferably 430° C.≤T≤530° C., for a period of time t where t≥5 minutes, preferably 10 minutes≤t≤40 minutes.

These short contact times in the region of up to 40 minutes are in principle sufficient to create the desired surface compressive stress in the surface region. If, however, an increase in strength in the form body down to a depth of 20 µm or more is desired, then longer contact times will be required, for example 6 or 10 hours, depending on the temperature at the time of contact with the paste.

In a preferred manner the form body is annealed in a paste containing potassium ions, in particular a paste containing $KNO_3$, KCl or $K_2CO_3$, or a paste containing sodium ions, in particular in a paste containing $NaNO_3$, sodium acetate or sodium salts of organic acids, or in a paste containing a mixture of potassium ions and sodium ions, in particular at a ratio of 50:50 mol. %, preferably in a paste containing $NaNO_3$ and $KNO_3$.

It is preferred for the form body or a blank, from which the form body is derived, to be fabricated from a glass melt, which contains as the starting components at least: $SiO_2$, $Al_2O_3$, $Li_2O$, $K_2O$, at least one nucleating agent, such as $P_2O_5$, and at least one stabilizer such as $ZrO_2$.

The invention is characterized in a particular manner in that not only are lithium ions replaced by larger alkali ions, in particular through potassium and/or sodium ions, but also that to increase strength in the starting substance and thus in the glass phase of the form body/blank from which the form body is derived, at least one dissolved stabilizer, in particular in the form of $ZrO_2$, is contained, wherein the concentration is preferably in the range of 8 to 12% by weight with reference to the initial composition.

In particular the invention is characterized in that the form body/blank is fabricated from a glass melt that has the following composition in percentage by weight:
- $SiO_2$ 50-80, preferably 52-70, especially preferred 56-61
- at least one nucleating agent, such as $P_2O_5$, 0.5-11, preferably 3-8, especially preferred 4-7
- $Al_2O_3$ 0-10, preferably 0.5-5, especially preferred 1.5-3.2
- $Li_2O$ 10-25, preferably 13-22, especially preferred 14-21
- $K_2O$ 0-13, preferably 0.5-8, especially preferred 1.0-2.5
- $Na_2O$ 0-1, preferably 0-0.5, especially preferred 0.2-0.5
- $ZrO_2$ 0-20, preferably 4-16, in particular 6-14, especially preferred 8-12
- $CeO_2$ 0-10, preferably 0.5-8, especially preferred 1.0-2.5
- $Tb_4O_7$ 0-8, preferably 0.5-6, especially preferred 1.0 to 2.0
- optionally an oxide or a number of oxides of an earth alkali metal or a number of earth alkali metals from the group magnesium, calcium, strontium and barium 0-20, preferably 0-10, especially preferred 0-5,
- optionally one or more additives from the group $B_2O_3$, $MnO_2$, $Fe_2O_3$, $V_2O_5$, $TiO_2$, $Sb_2O_3$, ZnO, $SnO_2$ and fluorides 0-6, preferably 0-4
- optionally one or more oxides of the rare earth metals with the atomic numbers 57, 59-64, 66-71, in particular lanthanum, yttrium, praseodymium, erbium, and europium, 0-5, preferably 0-3 wherein the total sum is 100% by weight.

"Optionally an oxide or a number of oxides" means that it is not absolutely necessary for one or more oxides to be contained in the glass melt.

In particular the body/blank has the following composition in percentage by weight:

| | |
|---|---|
| $SiO_2$ | 58.1 ± 2.0 |
| $P_2O_5$ | 5.0 ± 1.5 |
| $Al_2O_3$ | 4.0 ± 2.5 |
| $Li_2O$ | 16.5 ± 4.0 |
| $K_2O$ | 2.0 ± 0.2 |
| $ZrO_2$ | 10.0 ± 0.5 |
| $CeO_2$ | 0-3, preferably 1.5 ± 0.6 |
| $Tb_4O_7$ | 0-3, preferably 1.2 ± 0.4, |
| $Na_2O$ | 0-0.5, preferably 0.2-0.5 | wherein the total sum is 100% by weight.

In embodiment the invention is characterized in that the blank is formed from the glass melt during cooling or after cooling to room temperature, with the blank then undergoing at least a first heat treatment W1 at a temperature $T_{W1}$ over a period of time $t_{W1}$, wherein 620° C.≤$T_{W1}$≤800° C., in particular 650° C.≤$T_{W1}$≤750° C., and/or 1 minute≤$t_{W1}$≤200 minutes, preferably 10 minutes≤$t_{W1}$≤60 minutes. The form body is fabricated from the blank/heat-treated blank.

A corresponding lithium silicate glass ceramic blank can be worked without difficulty, with minimal tool wear. A corresponding blank can also be pressed in a desired geometry.

In particular to achieve a final crystallization it is provided for the lithium silicate glass ceramic blank after the first heat treatment W1 to undergo a second heat treatment W2 at a temperature $T_{W2}$ for a period of time $t_{W2}$, wherein 800° C.≤$T_{W2}$≤1040° C., preferably 800° C.≤$T_{W2}$≤900° C. and/or 2 minutes≤$t_{W2}$≤200 minutes, preferably 3 minutes≤$t_{W2}$≤30 minutes.

The following temperature values and heating rates are preferably chosen for the heat treatment steps leading to a pre-crystallization/final crystallization. With regard to the first heat treatment W1 it is in particular provided for a two-step approach, wherein a first holding stage is in the range 640° C. to 680° C. and a second holding stage is in the range 720° C. to 780° C. In each stage the heated blank is held at a temperature for a period of time; in the first stage this is preferably between 35 and 45 minutes and in the second stage preferably between 15 and 25 minutes.

According to the invention it is in particular also provided for the glass phase to be 20-65% by volume, in particular 40-60% by volume.

The invention is consequently also characterized by a form body in which the lithium silicate crystals are present in the range 35-80% by volume and in particular 40-60% by volume. Lithium silicate crystals here mean the sum of lithium disilicate crystals, lithium metasilicate crystals and lithium phosphate crystals if $P_2O_5$ is contained.

The blank is worked through grinding or milling either after the first heat treatment stage or after the second heat treatment stage, but preferably after the second heat treatment stage to obtain the form body of the desired geometry.

This is then given a glaze firing—without application of a glaze—or is polished by hand. The same applies if the form body is derived through pressing.

The available form body is then covered with a paste that contains the required alkali metal ions, in particular Na ions and/or K ions.

Following cooling and the removal of any adhering residues of paste and if necessary to a certain degree working of the form body so made available it may be deployed, in particular as a dental restoration. In view of the increase in strength the form body may in particular be a multi-unit bridge.

Samples of corresponding form bodies have demonstrated that flexural strength values in excess of 800 MPa can be attained. The values were determined using the three-point method for flexural strength specified in DIN EN ISO 6872:2009-1.

The invention is characterized by the fact that the form body is coated or sprayed with a viscous sodium salt solution or sodium salt dispersion as the paste. For this it is in particular intended that sodium salts are mixed with at least one substance from the group 1,4-butanediol, hexanetriol or a mixture of the two substances.

In particular, an alkali metal salt, such as a sodium salt, in particular $NaNO_3$ salt with a mean particle size $d_{50} \leq 40$ µm, preferably $\leq 20$ µm, together with an organic liquid matrix such as 1,4-butanediol and/or hexanetriol are used as the paste. The hygroscopic behavior of sodium nitrate means that storage in normal ambient air for a longer period of time will result in an agglomeration of the salt. For this reason a sodium salt with a corresponding particle size is not offered commercially. It is therefore ground in a special step to prepare the commercial raw material in a suitable procedure using a ball mill or through wet grinding in alcohol.

Independently thereof, the paste is applied to the form body to a degree that all surfaces are covered, wherein in particular a thickness D of not less than 0.5 mm, preferably $1\ mm<D<3\ mm$, should be maintained. There is, however, no departure from the invention if not all surfaces are covered by the paste and/or one or more surfaces are not completely covered by the paste.

Further details, advantages and characteristics of the invention are derived not just from the claims and the characteristics to be drawn from them—either alone or in combination—but also from the examples given below.

In the tests described below at least raw materials, such as lithium carbonate, quartz, aluminum oxide, zirconium oxide, were mixed in a drum mixer until a visually uniform mixture resulted. The compositions according to the data of the manufacturers used for the tests are given below.

The following holds in principle for the tests given below:

The mixture in question was melted at a temperature of 1500° C. for a period of 5 hours in a high-temperature resistant platinum alloy crucible. The melt was subsequently poured into molds to derive rectangular bodies (blocks). The blocks were subsequently subjected to a two-step heat treatment, designated the first heat treatment step, to create lithium metasilicate crystals as the main crystal phase (1st treatment step). The blocks were thereby heated in the first heat treatment step W1 at a heating rate of 2 K/minute to 660° C. and held at that temperature for 40 minutes. They were then heated further to 750° C. at a heating rate of 10 K/minute. The specimens were held at that temperature for 20 minutes. This heat treatment influences nucleation and lithium metasilicate crystals are formed.

The blocks were then subjected to a second heat treatment step W2 (2nd treatment step) to form lithium disilicate crystals as the main crystal phase. In this heat treatment step the blocks were maintained at a temperature $T_2$ for a period of time $t_2$. The corresponding values are given below. They were then cooled to room temperature.

Bending rods (specimens) of rectangular shape were then derived by machine from the cooled blocks (3rd treatment step) through grinding of the blocks. The bending rods had the following dimensions: length 15 mm, width 4.1 mm and height 1.2 mm. The edges of some of the specimens were then smoothed, using silicon carbide abrasive paper with a granulation of 1200. A Struers Knuth-Rotor rotary grinding machine was used for grinding. The sides of the specimens were then ground (4th treatment step). Here too, a SiC abrasive paper with a granulation of 1200 was used.

The three-point flexural strength measurements were carried out as specified in DIN EN ISO 6872:2009-01. For this purpose the specimens (small rods) were mounted on two supports at a distance of 10 mm apart. A loading piston acted with 0.5 mm/min on the specimens between the rods, with the tip in contact with the specimen having a radius of 0.8 mm.

Example 1 (Lithium Silicate Glass Ceramic According to the Invention)

The following starting composition (in percentage by weight) according to manufacturer specifications was used to derive lithium silicate glass and from that lithium silicate glass ceramic material to carry out a number of tests.

| | |
|---|---|
| $SiO_2$ | 58.1-59.1 |
| $P_2O_5$ | 5.8-5.9 |
| $Al_2O_3$ | 1.9-2.0 |
| $Li_2O$ | 18.5-18.8 |
| $K_2O$ | 1.9-2.0 |
| $ZrO_2$ | 9.5-10.5 |
| $CeO_2$ | 1.0-2.0 |
| $Tb_4O_7$ | 1.0-1.5 |
| $Na_2O$ | 0-0.2 |

The percentage of glass phase was in the range 40-60% by volume.

a) Test Series #1

Twenty rods were first prepared and treatment steps 1-4 carried out for them. The final crystallization (second heat treatment step) was carried out at a temperature $T_2=830°$ C. for a period of time $t_2=5$ minutes.

Five of these rods were subjected, without further treatment, to a three-point flexural strength test. A mean value of 289 MPa was obtained.

Five rods were coated with a paste which contained a commercially-available sodium nitrate without a specified particle size distribution as the starting salt, which was in an organic liquid matrix of 1,4-butanediol. The paste layer thickness was 2 mm. The specimens were then annealed in a Ney-Vulcan burn-out oven for 20 minutes at a temperature of 480° C. The specimens were then cooled and paste residues removed by immersing them in an ultrasound bath containing de-ionized water for up to 5 minutes. Three-point flexural strength measurements were then carried out as described. The mean three-point flexural strength value was 489 MPa. The remaining 10 rods were treated identically and tested in a different test facility. The mean three-point flexural strength value for them was 526 MPa.

b) Test Series #2

In conformance with test series #1 and with the aforementioned comparative values for untreated specimens applying, a further 10 specimens were prepared. These were coated with a paste which contained the same commercially-available sodium nitrate without a specified particle size distribution as the starting salt, in an organic liquid matrix of 1,4-butanediol. The paste layer thickness was 2 mm. The specimens were then annealed in an Austromat 3001 ceramic press furnace for a period of 20 minutes at a temperature of 480° C. The specimens were then cooled and paste residues removed by immersing them in an ultrasound bath containing de-ionized water for up to 5 minutes. Three-point flexural strength measurements were then carried out as described. The mean three-point flexural strength value was 556 MPa.

c) Test Series #3

Thirty rods were prepared from the starting materials given above. They were then coated with a paste which contained a commercially-available potassium nitrate without a specified particle size distribution as the starting salt, in an organic liquid matrix of 1,4-butanediol. The paste layer thickness was 2 mm. Ten of these specimens were then annealed in an Austromat 2001 ceramic press furnace for 20 minutes, 30 minutes and 40 minutes at a temperature of 480° C. The specimens were then cooled and paste residues removed by immersing them in an ultrasound bath containing de-ionized water for up to 5 minutes. Three-point flexural strength measurements were then carried out as described. The mean three-point flexural strength value was 377 MPa after 20 minutes, 376 MPa after 30 minutes and 426 MPa after 40 minutes.

d) Test Series #4

Fifteen rods were prepared from the starting materials given above. They were coated with a paste that contained sodium nitrate as the starting salt, and which was passed through a sieve to reduce the particle size to below 31 μm and which was contained in an organic liquid matrix of 1,4-butanediol and hexanetriol. The layer thickness of the paste was 2 mm. Ten of the specimens were annealed in an Austromat 3001 ceramic press furnace for a period of 20 minutes at a temperature of 480° C. The specimens were then cooled and residues of paste removed through immersion in an ultrasound bath containing de-ionized water for up to 5 minutes. Five of the specimens were heated in the same furnace without paste at 480° C. for 20 minutes (reference specimens) and also cleaned in an ultrasound bath for up to 5 minutes. Three-point flexural strength measurements were then carried out as described above. The mean three-point flexural strength value was 312 MPa without paste, and 624 MPa after annealing in the paste. All of the individual values after coating with the paste were above 500 MPa, with maximum values up to 766 MPa. When specimens were prepared by comparable means and annealed in a pure sodium nitrate melt at 480° C. for 20 minutes the mean flexural strength value was 620 MPa, with one individual value below 500 MPa.

e) Test Series #5

Ten full-anatomical crowns of a lithium silicate material of the previously described composition were prepared and polished to a high gloss by dental technology methods. Five of these crowns were coated with a paste which contained a commercially-available sodium nitrate without a specified particle size distribution as the starting salt, and which was in an organic liquid matrix of 1,4-butanediol. The paste layer thickness was 2 mm. The specimens were then annealed in a Ney-Vulcan burn-out oven for 20 minutes at a temperature of 480° C. The specimens were then cooled and paste residues removed by immersing them in an ultrasound bath containing de-ionized water for up to 5 minutes. The crowns were then placed on titanium stumps and cemented. In a simple pressure test they were loaded with a steel ball until break point. The average breaking load for five untreated crowns was 2106 N and for the treated specimens it was 3714 N.

It is apparent from these tests that the use of the paste with sodium ions can lead to an increase in the three-point flexural strength to a value above 500 MPa. There was also a marked increase in strength using full-anatomical crowns in a test that was close to real conditions after annealing for just 20 minutes. The variation from the mean value exhibited by the absolute values is the result of the statistical error distribution in ceramics, which is the cause of breaks.

Example #2 (Lithium Silicate Glass Ceramic According to the Invention)

A lithium silicate material of the following composition in percentage by weight was melted as described above:

| | |
|---|---|
| $SiO_2$ | 56.0-59.5 |
| $P_2O_5$ | 4.0-6.0 |
| $Al_2O_3$ | 2.5-5.5 |
| $Li_2O$ | 13.0-15.0 |
| $K_2O$ | 1.0-2.0 |
| $ZrO_2$ | 9.5-10.5 |
| $CeO_2$ | 1.0-2.0 |
| $Tb_4O_7$ | 1.0-1.2 |
| $Na_2O$ | 0.2-0.5 |

The glass phase percentage was in the range 40-60% by volume.

The melted material was poured into molds of platinum to derive round rods (pellets) for pressing in a dental furnace for pressed ceramics. A cavity of rectangular shape was thereby formed in an investment material to provide specimen rods for measurements. The dimensions of the rods corresponded to those for test series a) to e). The material to be pressed was pressed in the investment material at a temperature of 860° C. for 30 minutes. The rods were then removed from the investment material using aluminum oxide particles of mean diameter 110 μm with a jet pressure between 1 and 1.5 bar to keep possible damage low. The edges were then smoothed in accordance with test series a), b) and c) and the surfaces polished (4th treatment step). The remaining specimens were then annealed in a paste of sodium salts and 1,4-butanediol.

f) Test Series #6

Ten specimens were prepared analogously to test series a)-c). Five untreated specimens had a mean three-point flexural strength value of 335 MPa. The other five specimens were coated with a paste which contained a commercially-available sodium nitrate without a specified particle size distribution as the starting salt, which was in an organic liquid matrix of 1,4-butanediol. The paste layer thickness was 2 mm. The specimens were then annealed in a Ney-Vulcan burn-out furnace for 15 minutes at a temperature of 480° C. The specimens were then cooled and paste residues removed by immersing them in an ultrasound bath containing de-ionized water for up to 5 minutes. Three-point flexural strength measurements were then carried out as described above. The mean three-point flexural strength value was 385 MPa.

g) Test Series #7

Five specimens were prepared analogously to test series a)-c). The comparative values for untreated specimens from test series e) thus also apply here. The specimens were coated with a paste which contained a commercially-available sodium nitrate without a specified particle size distribution as the starting salt, which was in an organic liquid matrix of 1,4-butanediol. The paste layer thickness was 2 mm. The specimens were then annealed in a Ney-Vulcan burn-out furnace for 20 minutes at a temperature of 480° C. The specimens were then cooled and paste residues removed by immersing them in an ultrasound bath containing deionized water for up to 5 minutes. Three-point flexural strength measurements were then carried out as described above. The mean three-point flexural strength value was 463 MPa.

Five further rods were treated identically and tested in a different test facility. The mean three-point flexural strength was 420 MPa.

It is evident that in comparison to test series a)-c) with similar starting materials there was not a marked increase in strength in each case.

The fluctuation in the starting strength value is attributable to the different batches and the nature of the preparation of the specimens.

Example #3 (Glass Ceramic of the State of the Art)

Commercial pellets for pressing in a dental furnace for pressing ceramics were used. Analysis of the pellets revealed the following composition in percentage by weight:

| | |
|---|---|
| $SiO_2$ | 65.0-72.0 |
| $P_2O_5$ | 2.5-5.0 |
| $Al_2O_3$ | 1.5-3.5 |
| $Li_2O$ | 12.0-15.5 |
| $K_2O$ | 3.0-4.0 |
| $ZrO_2$ | 0-1.5 |
| $CeO_2$ | 0.5-2.3 |
| $Tb_4O_7$ | 0.5-1.0 |
| $Na_2O$ | 0-0.1 |

The glass phase percentage was 5-15% by volume.

The corresponding pellets were pressed in the dental furnace for 30 minutes at a temperature of 920° C. The edges were then smoothed and a polishing carried out.

h) Test Series #8

Measurements for 9 untreated specimens yielded a mean flexural strength of 422 MPa.

Ten specimens, treated identically, were annealed in a technically-pure $NaNO_3$ melt for 20 minutes at 480° C. The mean flexural strength after annealing was 358 MPa.

Example #4 (Glass Ceramic According to the State of the Art)

Commercially available blocks of lithium silicate glass ceramic of the following composition in percentage by weight according to analysis were used:

| | |
|---|---|
| $SiO_2$ | 65.0-72.0 |
| $P_2O_5$ | 2.5-5.0 |
| $Al_2O_3$ | 1.5-3.5 |
| $Li_2O$ | 12.0-15.5 |
| $K_2O$ | 3.0-4.0 |
| $ZrO_2$ | 0-1.5 |
| $CeO_2$ | 0.5-2.3 |
| $Tb_4O_7$ | 0.5-1.0 |
| $Na_2O$ | 0-0.1 |

The percentage of the glass phase was 5-15% by volume.

As for Example 1 specimen rods of corresponding dimensions were prepared through grinding of the blocks (form bodies), with their edges smoothed and subsequent polishing of the surfaces.

For the final crystallization, the specimens were heated at 850° C. for a period of 10 minutes according to the manufacturer's instructions.

The mean strength value for 11 specimens that were not annealed was 381 MPa.

Ten specimens were annealed in a technically-pure $NaNO_3$ melt for 20 minutes at 480° C. The mean strength value was 348 MPa.

A comparison of the examples/test series shows that at a low total alkali oxide content in the glass phase of the specimens, i.e., after performance of the crystallization, and with a high glass percentage in the ceramic material, lithium ions can be replaced by other alkali ions of greater diameter, so that the desired surface compressive stress is created with a consequent increase in strength. This effect is reduced or not seen at all if the percentage of the glass phase in the form body to be used, is below 20%, in particular below 15%, as is clear from examples 3 and 4. A possible reason for this—possibly independently of the glass phase percentage—is that the alkali oxide content, i.e., the content of sodium oxide and potassium oxide, in the glass phase is more than 2.5% by weight and in particular more than 3% by weight of the starting composition. The percentage of $Li_2O$ in the starting composition is also likely to have an influence, i.e., a higher lithium ion percentage enables an increased exchange of sodium and potassium ions against lithium ions so that the compressive surface stress is increased.

A possible explanation is as follows. The ion exchange causing the surface compressive stress takes place at the interface between the surface of the glass ceramic specimens and the salt, wherein the process is controlled through the diffusion of alkali ions of the glass ceramic. Lithium ions diffuse from the glass ceramic to the surface where they are replaced by alkali ions from the salt and alkali ions from the salt diffuse after replacing lithium ions from the surface into the internal region of the glass ceramic. If the glass phase percentage in the lithium silicate glass ceramic is high and prior to annealing there is a relatively low percentage of potassium ions and sodium ions in the glass phase, then the driving force and thus the potential for ion exchange will be higher/more effective in comparison to glass ceramic materials in which the glass phase percentage is low and the original alkali ion percentage (sodium oxide and potassium oxide) in the glass phase is relatively high.

This may be additionally intensified by the higher lithium ion percentage in the glass phase, i.e., the lithium ion percentage that is not bound in precipitates and which is therefore available for ion exchange. The precipitates are Li—Si and Li—P precipitates.

Irrespective of the inclusion of the potassium ions compared to specimens that had not been annealed in a salt paste containing potassium ions there were no differences in the microstructure upon examination using a scanning electron microscope.

It follows from the above that according to the teaching a surface compressive stress is generated when lithium ions are replaced by alkali metal ions of greater diameter. To bring about an increase in strength for form parts that are of a lithium silicate glass ceramic material, different measures according to the invention are proposed and explained with reference to FIG. 1.

To facilitate an increase in surface strength in a dental form body such as a crown 10 through the creation of a surface compressive stress, by means of the replacement of lithium ions in the crown 10 of lithium silicate glass ceramic by alkali metal ions of greater diameter, it is envisaged that the crown 10 is enveloped on all sides by a paste 12 that comprises an alkali metal salt or contains an alkali metal salt. To derive the paste a corresponding salt/salt mixture with 1,4-butanediol or hexanetriol or a mixture thereof is mixed to yield a salt solution of the desired viscosity, in particular a highly viscous and thus thick salt solution/dispersion. The crown 10 coated in this manner with the paste 12 is then subjected to heat treatment for a period of time. For this purpose the crown 10 is heated in a common ceramic firing furnace used in dental laboratories for a period of time t in the range 10-40 minutes at a temperature in the range 430-530° C. After cooling, the paste which remains as a crust on the crown 10 is removed in particular using de-ionized water in an ultrasound bath for a maximum of 10 minutes. No further treatment steps, in particular heat treatment steps above 200° C., are carried out to rule out the possibility of alkali metal ions, in particular sodium ions and/or potassium ions, diffusing from the surface layer of the crown 10 into the internal region.

The invention claimed is:

1. A method to increase the strength of a medical form body of lithium silicate glass ceramic comprising the steps of:
preparing the form body or a blank from a glass melt that includes at least the following as starting components: $SiO_2$, $Al_2O_3$, $Li_2O$, $K_2O$, at least one nucleating agent, and at least one stabilizer;
forming the blank from the glass melt during the course of cooling or following cooling to room temperature, said blank then being subject to at least one first heat treatment W1 at a temperature $T_{W1}$ for a time $t_{W1}$, wherein 620° C.$\leq T_{W1} \leq$800° C., and/or 1 minute$\leq t_{W1} \leq$200 minutes;
mixing a viscous solution or dispersion of a salt that includes alkali metal ions with at least one substance selected from the group consisting of 1,4-butanediol, hexanetriol, and a mixture of the two substances to form the paste;
coating at least a portion of the form body with the paste having one or more alkali metals, wherein the at least portion of the form body is in contact with the paste for a time t where t>5 minutes at a temperature T where T≥300° C. so that a surface compressive stress is created in the form body of lithium silicate glass ceramic through the replacement of lithium ions by alkali metal ions of greater diameter; and
removing the paste from the form body;
wherein alkali metal ions are selected from the group consisting of Na, K, Cs, Rb ions and combinations thereof to generate the surface compressive stress.

2. The method according to claim 1, wherein the coating step, the paste is applied to the form body by spraying on to the form body.

3. The method according to claim 1, wherein the coating step, the paste is applied to all surfaces of the form body with a thickness D of not less than 0.5 mm.

4. The method according to claim 1, wherein the paste includes potassium ions, sodium ions or a combination of both potassium ions and sodium ions.

5. The method according to claim 1, wherein the glass melt further includes at least one coloring metal oxide.

6. The method according to claim 1, wherein the step of forming the form body or a blank from the glass melt includes the following components in percentage by weight:

| | |
|---|---|
| $SiO_2$ | 50-80, | at least one nucleating agent 0.5-11,

| | |
|---|---|
| $Al_2O_3$ | 0-10, |
| $Li_2O$ | 10-25, |
| $K_2O$ | 0-13, |
| $Na_2O$ | 0-1, |
| $ZrO_2$ | 0-20, |
| $CeO_2$ | 0-10, |
| $Tb_4O_7$ | 0-8, | optionally an oxide or a number of oxides of an earth alkali metal or a number of earth alkali metals selected from the group consisting of magnesium, calcium, strontium, and barium 0-20,
optionally one or more additives selected from the group consisting of $B_2O_3$, $MnO_2$, $Fe_2O_3$, $V_2O_5$, $TiO_2$, $Sb_2O_3$, ZnO, $SnO_2$ and fluorides 0-6,
optionally one or more oxides of the rare earth metals with the atomic numbers 57, 59-64, 66-71 0-5.

7. The method according to claim 1, wherein the glass melt includes the following as starting components in percentage by weight

| | |
|---|---|
| $SiO_2$ | 58.1 ± 2.0 |
| $P_2O_5$ | 5.0 ± 1.5 |
| $Al_2O_3$ | 4.0 ± 2.5 |
| $Li_2O$ | 16.5 ± 4.0 |
| $K_2O$ | 2.0 ± 0.2 |
| $ZrO_2$ | 10.0 ± 0.5 |
| $CeO_2$ | 0-3, |
| $Tb_4O_7$ | 0-3, |
| $Na_2O$ | 0-0.5. |

8. The method according to claim 1, wherein the forming step, the first heat treatment W1 is carried out in two steps, wherein in particular in a first step a temperature $T_{St1}$ is set where 630° C.$\leq T_{St1} \leq$690° C. and/or in a second step a temperature $T_{St2}$ where 720° C.$\leq T_{St2} \leq$780° C. and/or a heating rate $A_{St1}$ up to the temperature $T_{St1}$ is 1.5 K/minute$\leq A_{St1} \leq$2.5 K/minute and/or a heating rate $A_{St2}$ up to the temperature $T_{St2}$ is 8 K/minute$\leq T_{St2} \leq$12 K/minute.

9. The method according to claim 1, wherein the forming step, the lithium silicate glass ceramic blank is subjected, after the first heat treatment W1, to a second heat treatment W2 at a temperature $T_{W2}$ for a time $t_{W2}$, wherein 800° C.$\leq T_{W2} \leq$1040° C., and/or 2 minutes$\leq t_{W2} \leq$200 minutes.

10. The method according to claim 1, wherein the forming step, after the first or second heat treatment step, the form body is prepared from the blank through grinding and/or milling or pressing, wherein the heat treatment step or steps is/are carried out during or after pressing.

11. Use of a paste containing at least one alkali metal salt for coating a form body of lithium silicate glass ceramic material, according to claim 1.

* * * * *